US008835827B2

(12) United States Patent
Leijssen et al.

(10) Patent No.: US 8,835,827 B2
(45) Date of Patent: Sep. 16, 2014

(54) CURRENT INTEGRATOR WITH WIDE DYNAMIC RANGE

(75) Inventors: Jacobus Josephus Leijssen, Eindhoven (NL); Harry Marinus, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 880 days.

(21) Appl. No.: 12/741,042

(22) PCT Filed: Oct. 31, 2008

(86) PCT No.: PCT/IB2008/054544
§ 371 (c)(1),
(2), (4) Date: May 3, 2010

(87) PCT Pub. No.: WO2009/060361
PCT Pub. Date: May 14, 2009

(65) Prior Publication Data
US 2010/0253321 A1    Oct. 7, 2010

(30) Foreign Application Priority Data

Nov. 5, 2007  (EP) .................................... 07119980

(51) Int. Cl.
*H03G 3/20*  (2006.01)
(52) U.S. Cl.
USPC ............. 250/214 AG; 250/214 R; 250/214 C; 250/214 DC; 250/214 RC; 324/96; 324/428
(58) Field of Classification Search
USPC ......... 324/98, 427–428; 250/214 R–214 SW; 320/149
See application file for complete search history.

(56) References Cited

U.S. PATENT DOCUMENTS

| 5,933,305 | A | | 8/1999 | Schmalz et al. |
| 5,998,971 | A | | 12/1999 | Corbridge |
| 6,054,861 | A | * | 4/2000 | Takahashi ..................... 324/428 |
| 6,150,649 | A | | 11/2000 | Wake et al. |
| 6,157,170 | A | | 12/2000 | Noda et al. |
| 6,429,718 | B1 | | 8/2002 | Lauter et al. |
| 6,768,294 | B1 | * | 7/2004 | Moldavsky et al. ........ 324/76.39 |
| 7,709,778 | B2 | * | 5/2010 | Teeter et al. ............... 250/214 R |
| 7,714,268 | B2 | * | 5/2010 | Leijssen et al. ........... 250/214 R |
| 7,884,330 | B2 | * | 2/2011 | Leijssen et al. ........... 250/363.03 |
| 8,134,352 | B2 | * | 3/2012 | Van Der Wal et al. ........ 323/272 |
| 8,263,925 | B2 | * | 9/2012 | Decaens .................... 250/214 R |
| 8,358,103 | B2 | * | 1/2013 | Eastlack ....................... 320/108 |
| 2003/0076432 | A1 | * | 4/2003 | Luo et al. ...................... 348/308 |
| 2008/0048100 | A1 | * | 2/2008 | Bamji et al. ............... 250/214 A |
| 2010/0253321 | A1 | * | 10/2010 | Leijssen et al. ................. 324/98 |

FOREIGN PATENT DOCUMENTS

| WO | 03071291 | A1 | 8/2003 |
| WO | 2007029191 | A2 | 3/2007 |

* cited by examiner

*Primary Examiner* — Huy Q Phan
*Assistant Examiner* — Adam Clarke (57) ABSTRACT

A determination circuit for measuring a current is reset each time the integration value of the current exceeds a threshold until expiration of a predefined maximum integration time. This increases the accuracy of integrating a current and also increases the dynamic range of currents that can be integrated. To further increase the dynamic range of currents, the determination circuit may further include circuits having different gain factors.

3 Claims, 7 Drawing Sheets

| Diode current | Integrator 1 100pF Output to ADC | Integrator 2 100nF Output to ADC | Number of integrator 2 resets | Counter if 100MHz clock is used (10ns increments) |
|---|---|---|---|---|
| 1fA (< noise floor) | 1uV | Not used | 0 | 1000000 counts |
| 10fA (< noise floor) | 10uV | Not used | 0 | 1000000 counts |
| 100fA | 100uV | Not used | 0 | 1000000 counts |
| 1pA | 1mV | Not used | 0 | 1000000 counts |
| 10pA | 10mV | Not used | 0 | 1000000 counts |
| 100pA | 100mV | Not used | 0 | 1000000 counts |
| 1nA | 1V | Not used | 0 | 1000000 counts |
| 10nA | Limit reached = 10V | 10mV | 1 | 100000 counts |
| 33nA | Limit reached = 10V | 33mV | 1 | 33000 counts |
| 100nA | Limit reached = 10V | 100mV | 1 | 10000 counts |
| 1uA | Limit reached = 10V | 1V | 1 | 1000 counts |
| 2uA | Limit reached = 10V | 200mV | 1 | 100 counts |
| 3uA | Limit reached = 10V | 300mV | 1 | 10 counts |
| 10uA | Limit reached = 10V | 1V | 2 | 1 counts |
| 100uA | Limit reached = 10V | | 11 | |
| 1mA | Limit reached = 10V | | 101 | |
| 10mA | Limit reached = 10V | | 1001 | |
| 100mA | Limit reached = 10V | | 10001 | |
| 1A | Limit reached = 10V | | 100001 | |

FIG. 8

CURRENT INTEGRATOR WITH WIDE DYNAMIC RANGE

FIELD OF THE INVENTION

The invention relates to a determination circuit for measuring a current, the determination circuit comprising:
an integration unit for integrating a current over an integration time resulting in an integration value;
a time counter unit for counting the integration time from the start of integrating the current to a predefined maximum integration time.
The invention also relates to a method for measuring a current using such a determination circuit.
The invention also relates to a computer program product adapted, when being executed by a processor, to integrate a current using such a determination circuit.

BACKGROUND OF THE INVENTION

An embodiment of a determination circuit of this kind is known from the international patent application WO2007/029191 A2. In this document a determination circuit is described for measuring a low current with a large dynamic range, the determination circuit comprising an integration unit and a counter unit. The integration unit is adapted for integrating the current over an integration time, resulting in an integration value. The counter unit is adapted for counting the integration time, resulting in a counting value. The determination circuit is adapted for outputting a first measurement result on the basis of accounting value, if the integration value exceeds a first threshold value before expiration of a maximum integration time. The first threshold may be the saturation voltage of the integration unit comprising an operational amplifier with a capacitor connected to it in parallel. The first measurement result is the integration time needed for the integration value to exceed the first threshold. According to another embodiment, the determination circuit is adapted for outputting a second measurement result on the basis of the integration value, if the integration value is below the first threshold value at the expiration of the maximum integration time. According to yet another embodiment, the determination circuit is adapted for outputting a third measurement result on the basis of the counting value and the integration value, if the integration value exceeds in the first threshold value before the expiration of the maximum integration time and if the counting value is below a second threshold value. A determination circuit for integrating a current with a large dynamic range is useful in, for instance, a device for imaging an interior of an optically turbid medium using diffuse optical tomography. In such a device currents easily span 10 orders of magnitude.

SUMMARY OF THE INVENTION

It is an object of the invention to provide a determination circuit that is more precise than the determination circuit according to the prior art. According to the invention this object is realised in that the determination circuit further comprises:
a reset counter for counting the number of resets of the integration unit,
wherein the determination unit is adapted for:
(a) outputting a first measurement result if the absolute value of the integration value is below a reset threshold at the expiration of the predefined maximum integration time;
(b) resetting the integration unit if the absolute value of the integration value exceeds the reset threshold before the expiration of the predefined maximum integration time;
(c) repeating the steps of outputting and resetting each time the absolute value of the integration value exceeds the reset threshold until expiration of the predefined maximum integration time, counting the number of resets;
(d) outputting a second measurement result based on at least one of the integration value and the number of resets if the number of resets is nonzero.

The invention is based on the recognition that the invention allows a current that would saturate a determination circuit according to the prior art before expiration of the predefined maximum integration time to be integrated over a longer period of time. In fact, the current is integrated over a series of time intervals, each interval being separated from the previous interval by a reset of the integration unit. The fact that, with the invention, a current that would saturate a determination circuit according to the prior art can be integrated over a longer period of time means that a determination circuit according to the invention is more precise than a determination circuit according to the prior art. After all, it is generally known that the accuracy of a measurement increases as the time interval of all which a signal, in this case a current, is measured increases. Moreover, the integration values obtained for each time interval can be averaged, which also makes the determination circuit according to the invention more precise than a determination circuit according to the prior art, which bases its output on an integration over only a single interval as it cuts off the integration once the integration value exceeds the predetermined threshold.

It is an additional advantage of the invention that it has higher dynamic range of currents that can be integrated as compared to a determination circuit according to the prior art. If an integration unit comprised in a determination circuit according to the prior art saturates before expiration of the maximum integration time when integrating a certain current, a determination circuit according to the invention can continue integration by resetting the integration unit as many times as needed.

It is an additional advantage of the invention that it allows a capacitor to be chosen such that the determination circuit is optimised for a specific measuring range. One can, for instance, measure currents in the range 1 fA-1 µA (nine orders of magnitude) or in the range 1 pA-1 mA (also nine orders of magnitude). Whereas the first range is optimised for accurate measurements near the noise floor, the second range is optimised for larger currents.

Other documents that deal with measuring a current with a large dynamic range are U.S. Pat. No. 6,429,718 B1 and U.S. Pat. No. 6,150,649. However, neither of these documents describe resetting an integration unit (multiple times if needed) if the absolute value of the integration value generated by the integration unit exceeds a reset threshold and continuing integration of the current after the (or each) reset until expiration of a maximum integration time. In particular U.S. Pat. No. 6,429,718 B1 describes switching from one gain factor to another gain factor to enable integration of currents spanning a large dynamic range. U.S. Pat. No. 6,150,649 describes integrating currents spanning a large dynamic range over time intervals of different lengths to obtain different gains for currents of different magnitude.

An embodiment of the determination circuit according to the invention, wherein the integration unit comprises:

a higher gain integration circuit for integrating the current if the absolute value of the integration value lies below a switching threshold before expiration of the predefined maximum integration time;

a lower gain integration circuit for integrating the current until expiration of the predefined maximum integration time if the absolute value of the integration value generated by the higher gain integration circuit exceeds the switching threshold before expiration of the predefined maximum integration time. This embodiment has the advantage that it allows measurement of a current having a magnitude such that it causes the integration value generated by the higher gain integration circuit to exceed the switching threshold before expiration of the maximum integration time. As such this embodiment is suitable for measuring a current that would otherwise be too large to be measured without exceeding the switching threshold.

The object of the invention is also realised with a method for measuring a current with a large dynamic range, the method comprising the following steps:

integrating the current over a predefined maximum integration time using an integration unit, resulting in an integration value;

counting the integration time from the start of integrating the current to the expiration of the predefined maximum integration time;

outputting a first measurement result if the absolute value of the integration value is below a reset threshold at the expiration of the predefined maximum integration time;

resetting the integration unit if the absolute value of the integration value exceeds the reset threshold before the expiration of the predefined maximum integration time;

repeating the steps of outputting and resetting each time the absolute value of the integration value exceeds the reset threshold until expiration of the predefined maximum integration time, counting the number of resets;

outputting a second measurement result based on at least one of the integration value and the number of resets if the number of resets is nonzero.

An embodiment of the method according to the invention, wherein the method further comprises the following additional step:

switching the integration unit from a higher gain setting to a lower gain setting if the absolute value of the integration value generated in the higher gain setting exceeds a switching threshold before expiration of the predefined maximum integration time. Just as with the embodiment of the method discussed earlier, this embodiment has the advantage that it allows measurement of a current having a magnitude such that it causes the integration value generated by the higher gain integration circuit to exceed the switching threshold before expiration of the maximum integration time.

The object of the invention is also a realised with a computer program product adapted, when being executed by a processor, to carry out the following steps:

integrating a current over an integration time using an integration unit;

counting the integration time;

outputting a first measurement result if the absolute value of the integration value is below a reset threshold at the expiration of the predefined maximum integration time;

resetting the integration unit if the absolute value of the integration value exceeds the reset threshold before the expiration of the predefined maximum integration time;

repeating the steps of outputting and resetting each time the absolute value of the integration value exceeds the reset threshold until expiration of the predefined maximum integration time, counting the number of resets;

outputting a second measurement result based on at least one of the integration value and the number of resets if the number of resets is nonzero.

An embodiment of the computer program product according to the invention, wherein the computer program product is adapted, when being executed by a processor, to further carry out the following additional step:

switching the integration unit from a higher gain setting to a lower gain setting if the absolute value of the integration value generated in the higher gain setting exceeds a switching threshold before expiration of the predefined maximum integration time. Just as with the embodiment of the method discussed earlier, this embodiment has the advantage that it allows measurement of a current having a magnitude such that it causes the integration value generated by the higher gain integration circuit to exceed the switching threshold before expiration of the maximum integration time.

DETAILED DESCRIPTION OF EMBODIMENTS

Figure 1:
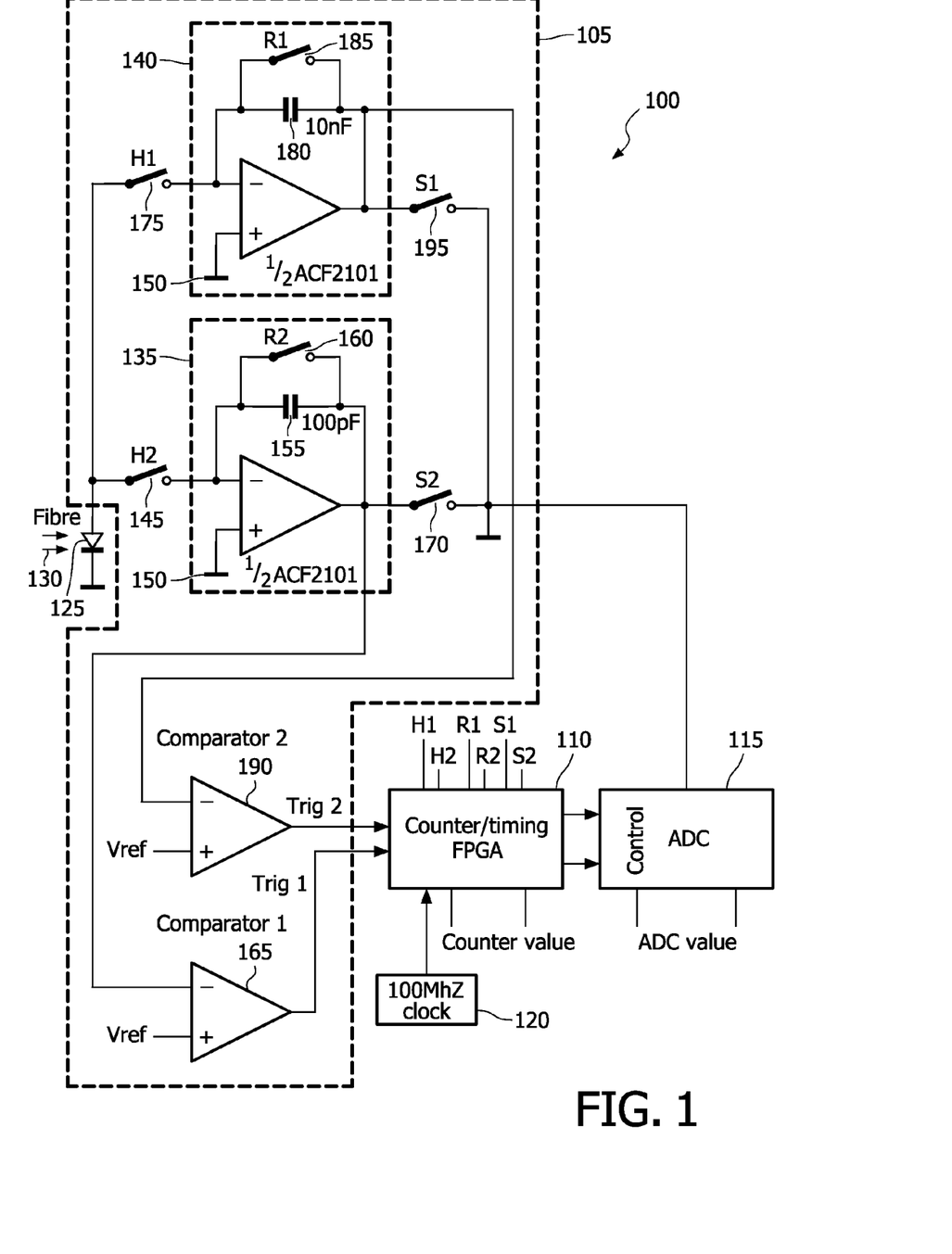
FIG. 1 schematically shows an embodiment of a determination circuit according to the invention comprising a higher gain circuit and a lower gain circuit.

FIG. 1 schematically shows an embodiment of a determination circuit according to the invention comprising a higher gain circuit and a lower gain circuit. The determination circuit 100 comprises an integration unit 105, a counter unit 110, an analog-to-digital converter 115, and a clock 120, such as a 100 MHz clock. However, different frequencies may be used for clocking. The counter unit 110 may be adapted as a counter/timing FPGA. FPGA is a Field Programmable Gate Array, a device with configurable digital logic, like counters, registers etc. The determination circuit 100 is adapted for measuring a current (or a plurality of currents) with a large dynamic range (for example a range spanning 10 decades or more). The current to be measured may be generated by a photodiode 125, which detects light from a light guide 130, such as an optical fibre. The light guide 130 may be comprised in a device for imaging an interior of an optically turbid medium using diffuse optical tomography. The integration unit 105 comprises a higher gain circuit 135 and a lower gain circuit 140. Both the higher gain circuit 135 and the lower gain circuit 140 may be adapted, for instance, as a 1/2ACF2101 or an IVC102. The higher gain circuit 135 is connected to switch 145 at its minus input. The plus input is connected to the ground 150. Furthermore, the minus input is connected to capacitor 155 (which may for example have a capacity of 100 pF) and (parallel to capacitor 155) switch 160 for performing a reset. The switch 160 is triggered by the R2 signal from the counter unit 110. The higher gain circuit 135 is connected to comparator 165. The comparator 165 compares the integration value generated by the higher gain circuit 135 to a reference voltage (the absolute value of the reference voltage forming the reset threshold). Switch 170 connects the higher gain circuit 135 to the analog-to-digital converter 115. The switch 170 is triggered by the S2 signal from the counter unit 110. Similarly, the lower gain circuit 140 is connected to switch 175 at its minus input. The plus input is connected to the ground 150. Furthermore, the minus input is connected to capacitor 180 (which may for example have a capacity of 10 nF) and (parallel to capacitor 180) switch 185 for performing a reset. The switch 185 is triggered by the R1 signal from the counter unit 110. The lower gain circuit 140 is connected to comparator 190. The comparator 190 compares the integration value generated by the lower gain circuit 140 to a reference voltage (the absolute value of the reference voltage forming the switching threshold). Switch 195 connects the lower gain circuit 140 to the analog-to-digital converter 115. The switch 195 is triggered by the S1 signal from the counter unit 110.

The current to be measured is input into the higher gain circuit 135 over switch 145, which is connected to the counter unit 110 and triggered by the H2 signal from the counter unit 110. The counter unit 110 counts the integration time with 10 ns increments (100 MHz clock). If the maximum integration time expires (for instance 100 ms) without the integration value exceeding the switching threshold, the value generated by the analog-to-digital converter 115 is used (see also FIG. 2). If the integration value exceeds the switching threshold before expiration of the maximum integration time, the current to be measured is input into the lower gain circuit 140 over switch 175, which is connected to the counter unit 110 and triggered by the H1 signal from the counter unit 110. The value of the counter unit 110 is latched and this value can be used as a result of the measurement (see also FIG. 3). If the lower gain circuit 140 is switched on and the integration value generated by the lower gain circuit 140 exceeds the reset threshold (as defined by the comparator 190) before expiration of the maximum integration time, the lower gain circuit 140 is reset by closing the switch 185, which is triggered by the R1 signal from the counter unit 110. After resetting the lower gain circuit 140, the lower gain circuit 140 continues to integrate the current to be measured and is reset each time the integration value exceeds the reset threshold as long as the maximum integration time has not expired. The total number of resets is counted by the counter unit 110. Counting the number of resets gives information about the measured current (see FIG. 4).

Clearly, it is possible to introduce at least one further integration circuit into the determination circuit 100 parallel to the higher gain circuit 135 and the lower gain circuit 140, each further integration circuit having a gain that is lower than the previously lowest gain. In this way, a cascade of circuits would be formed. A further integration circuit would allow a current being measured and the previously lowest gain circuit to be switched to the further integration circuit once integration value generated by the previously lowest gain circuit exceeds the switching threshold of that circuit. The switch from one circuit to the next would be similar to the switch from the higher gain circuit 135 to the lower gain circuit 140 once the integration value generated by the higher gain circuit 135 exceeds the switching threshold of the higher gain circuit 135. However, to obtain increasingly low gains, capacitors having increasingly large capacitances will be required. In practice, resetting increasingly large capacitances can become problematic. Consequently, a determination circuit 100 as shown in FIG. 1, with the lower gain circuit 140 being able to be reset multiple times, is a suitable alternative to a determination circuit comprising a cascade of increasingly lower gain circuits.

Moreover, it is clear that a determination circuit similar to the determination circuit 100 but comprising only a single gain circuit capable of being reset multiple times is also a possibility.

The determination circuit 100 enables to measure currents over an extremely wide dynamic range. Limitations are caused by the photodiode 125 rather than the integrator electronics.

Figure 2:
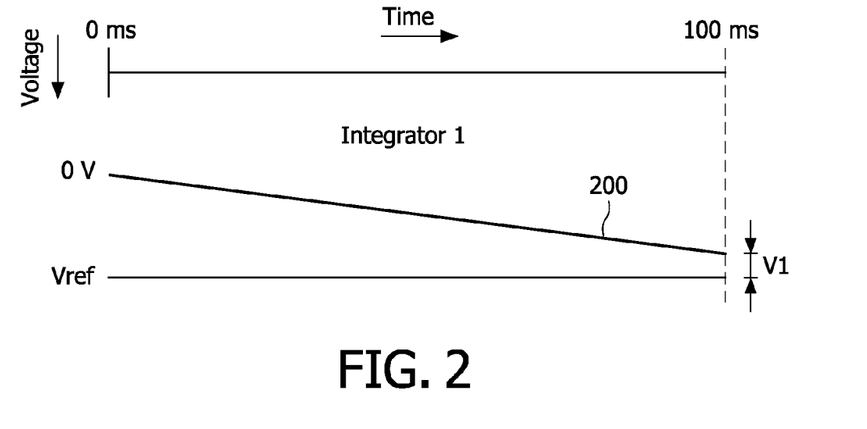
FIG. 2 schematically shows a lower current measurement using only the higher gain circuit.

FIG. 2 schematically shows a lower current measurement using only the higher gain circuit shown in FIG. 1. Plotted along the horizontal axis is a time interval representing the maximum integration time. In the example of FIG. 2 the maximum integration time is 100 ms. However, other values may be chosen depending on need. Along the vertical axis electronic potential is plotted, with 0 V representing the potential of the ground 150 (for the reference numbers the reader is referred to FIG. 1) and with Vref representing the reference potential used with the comparator 165 to define the reset threshold. During measurement of a low current, for instance a current of 800 pA, the integration value generated by the higher gain circuit 135 will not reach the reset threshold. The integration value as a function of time is indicated in FIG. 2 by the line 200. After expiration of the maximum integration time, V1 can be used as the measurement result.

Figure 3:
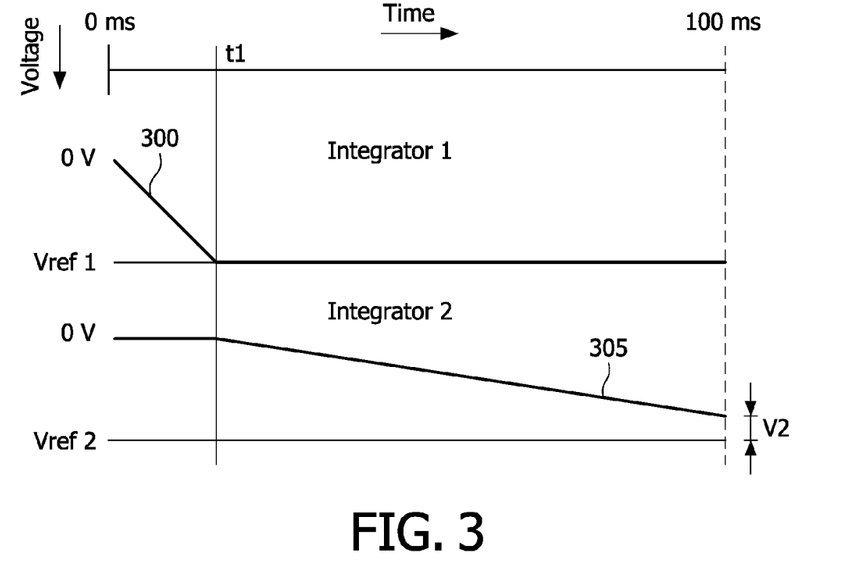
FIG. 3 schematically shows a higher current measurement using both a high against circuit and a lower gain circuit.

FIG. 3 schematically shows a higher current measurement using both the higher gain circuit and the lower gain circuit circuit shown in FIG. 1. Just as in FIG. 2, a time interval representing the maximum integration time is plotted along the horizontal axis. In the example of FIG. 3 the maximum integration time is 100 ms. However, other values may be chosen depending on need. Along the vertical axis electronic potential is plotted, with 0 V representing the potential of the ground 150 (for the reference numbers the reader is referred to FIG. 1), with Vref1 representing the reference potential used with the comparator 165 to define the switching threshold, and with Vref2 representing the reference potential used with the comparator 190 to define the reset threshold. At t1 the integration value generated by the higher gain circuit 135 and indicated by the line 300 exceeds the switching threshold. At that moment the lower gain circuit 140 is switched on. When the maximum integration time expires, the voltage output V2, based on the integration value generated by the lower gain circuit 140, is used as the measurement value. The integration value generated by the lower gain circuit 140 is a function of time is indicated by the line 305. The current measured in the example shown in FIG. 3 may, for instance, be 8 µA. This is 10,000 times the current that, by way of example, was measured in FIG. 2.

Figure 4:
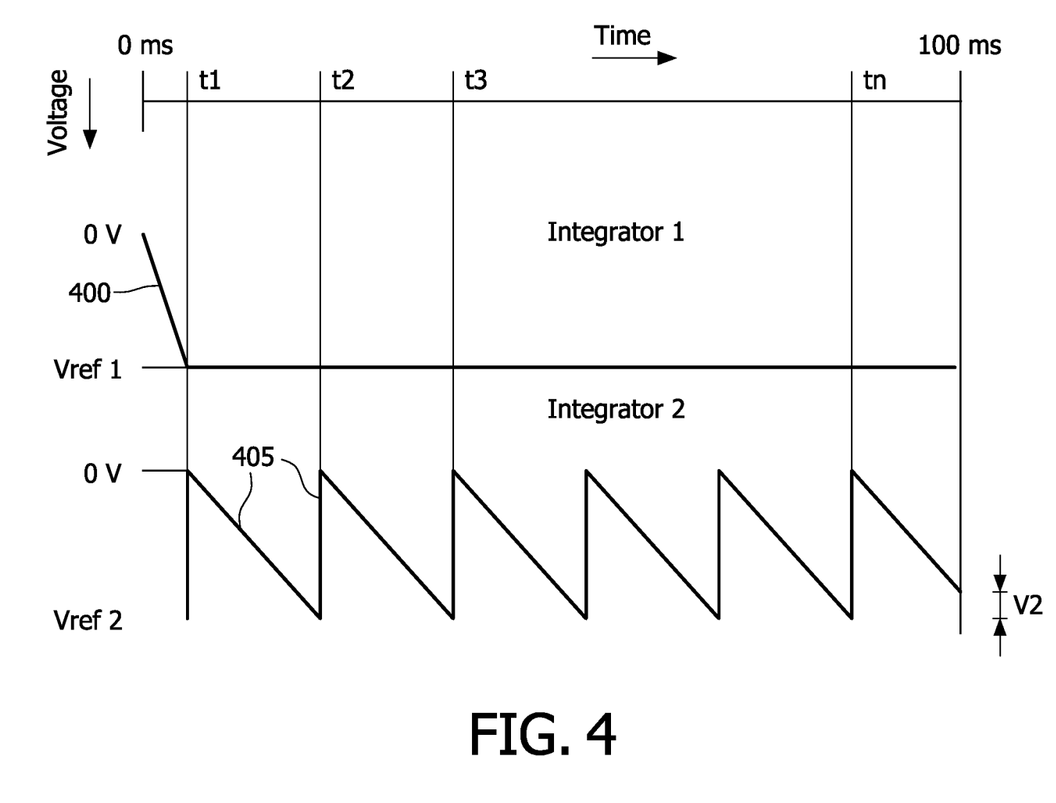
FIG. 4 schematically shows the timing of the multiple integration principle on a higher current.

FIG. 4 schematically shows the timing of the multiple integration principle on a higher current. Just as in the previous two figures, a time interval representing the maximum integration time is plotted along the horizontal axis. In the example of FIG. 4 the maximum integration time is 100 ms. However, other values may be chosen depending on need. Along the vertical axis electronic potential is plotted, with 0 V representing the potential of the ground 150 (for the reference numbers the reader is referred to FIG. 1), Vref1 representing the reference potential used with the comparator 165 to to define the switching threshold, and with Vref2 representing the reference potential used with the comparator 190 to define the reset threshold. At t1 the integration value generated by the higher gain circuit 135 and indicated by the line 400 reaches the switching threshold. At that moment, the lower gain circuit 140 is switched on. At t2 the integration value generated by the lower gain circuit 140 and indicated by the line 405 exceeds the reset threshold and the lower gain circuit 140 is reset. Following the reset, the lower gain circuit 140 continues to integrate the current until the maximum integration time expires. Again, the integration value generated by the lower gain circuit 140 as a function of time is indicated by the line 405. However, in FIG. 4 the lower gain circuit 140 reaches the reset threshold multiple times after the first reset and before expiration of the maximum integration time. Each time the lower gain circuit 140 reaches the reset threshold, it is reset until the maximum integration time expires. In the example of FIG. 4, the current measured by the lower gain circuit 140 equals six reset cycles minus V2.

Figure 5:
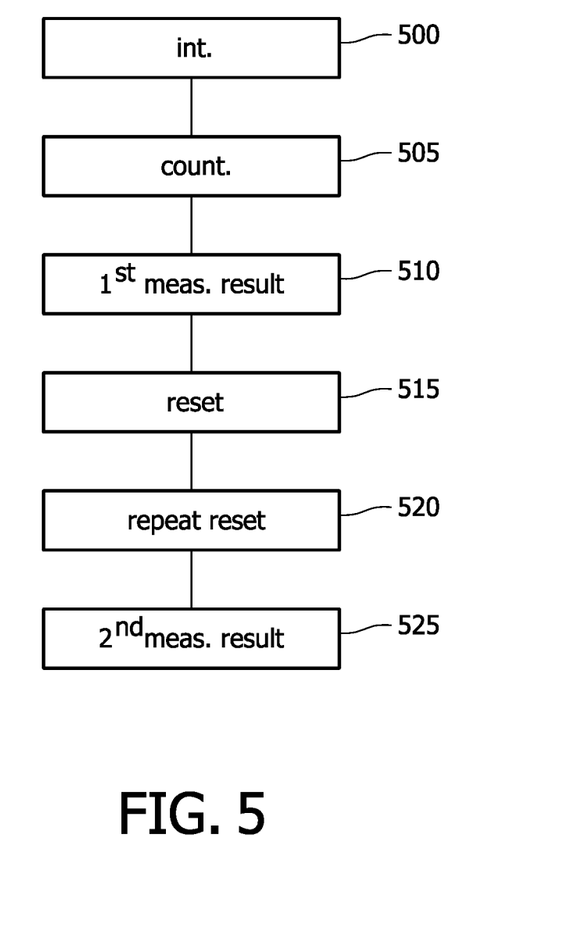
FIG. 5 schematically shows an embodiment of the method according to the invention.

FIG. 5 schematically shows an embodiment of the method according to the invention. In step 500 a current is integrated over a predefined maximum integration time using an integration unit. An embodiment of such an integration unit is comprised in the determination circuit 100 shown in FIG. 1. The integration results in integration value. In step 505 the time during which the current is integrated is counted from the start of the integration to the expiration of the maximum integration time. If the absolute value of the integration value is below a predetermined threshold at the expiration of the maximum integration time a first measurement result is output. This is done in step 510. If the absolute value of the integration value exceeds the predetermined threshold before the expiration of the maximum integration time, the integration unit is reset in step 515. Following the reset, the integration unit continues integrating the current. In step 520, step 515 is repeated until the maximum integration time expires, while counting the number of resets. Finally, in step 525, a second measurement result is output based on at least one of the integration value and the number of resets.

Figure 6:
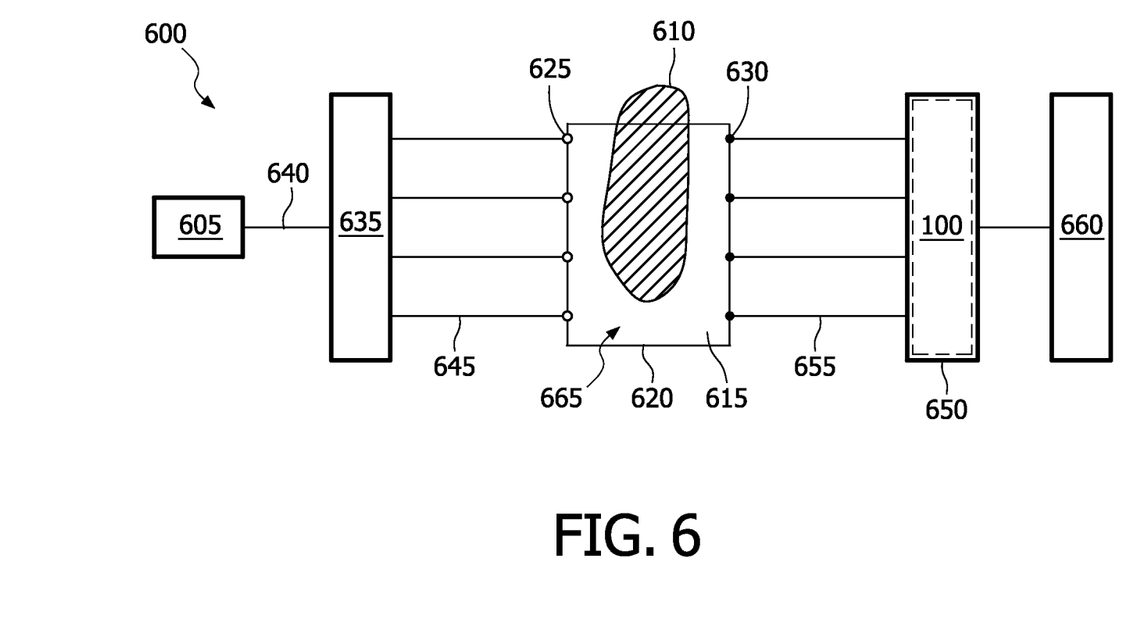
FIG. 6 schematically shows an embodiment of a device for imaging an interior of a turbid medium comprising a determination circuit according to the invention.

FIG. 6 schematically shows an embodiment of a device for imaging an interior of a turbid medium comprising a determination circuit according to the invention. The device 600 comprises a light source 605 for generating light to be coupled into the turbid medium 610. The turbid medium 610 is accommodated in a receiving volume 615, which is bounded by a receptacle 620. The receptacle 620 comprises a plurality of entrance positions for light 625 for coupling light from the light source 605 into the receiving volume 615. The receptacle 620 further comprises a plurality of collection positions for light 630 for collecting light emanating from the turbid medium 610 and, hence, from the receiving volume 615. The light source 605 is successively coupled to an entrance position for light chosen from the plurality of entrance positions for light 625 using an optical switch 630. The light source 605 is optically coupled to the optical switch 635 using light guide 640. The optical switch 635 is optically coupled to the receptacle 620 using light guides 645. In medical diagnostics a device such as the device 600 may be used for imaging an interior of a female breast. In that case, light generated by the light source 605 typically has a wavelength within the range of 400 nanometers to 1400 nanometers. Light emanating from the receptacle 620 at the plurality of collection positions for light 630 is coupled to a photodetector unit 650. The photodetector unit 650 is optically coupled to the receptacle 620 using light guides 655. The photodetector unit 650 comprises the determination circuit 100 shown in FIG. 1. Using the photodetector unit 650 light collected at the plurality of collection positions for light 630 is used to generate electronic signals representing the intensity of light emanating from the receptacle 620 at the plurality of collection positions for light 630. The based on the obtained electronic signals, an image of an interior of the turbid medium 610 is reconstructed using image reconstruction unit 660. The space inside the receptacle 620 not occupied by the turbid medium 610 may be filled with a matching medium 665 having optical properties, such as absorption and scattering coefficients, that substantially match the corresponding characteristics of the turbid medium 610. In this way, boundary artifacts stemming from coupling light into and out of the turbid medium 610 reduced. Moreover, use of a matching medium 665 prevents the occurrence of an optical short-circuit. An optical short-circuit occurs if light emanating at a collection position for light comprises both light that has passed through the turbid medium 610 and light that has passed through the receiving volume 615, but not through the turbid medium 610. As the turbid medium 610 strongly attenuates light that passes through it, light reaching a collection positions for light without having passed through the turbid medium 610 may dwarf the intensity of light that has passed through the turbid medium 610. This would hamper a proper measurement. When using a matching medium 665, the turbid medium 610 and the matching medium 665 effectively form a single turbid medium filling the receiving volume 615.

Figure 7:
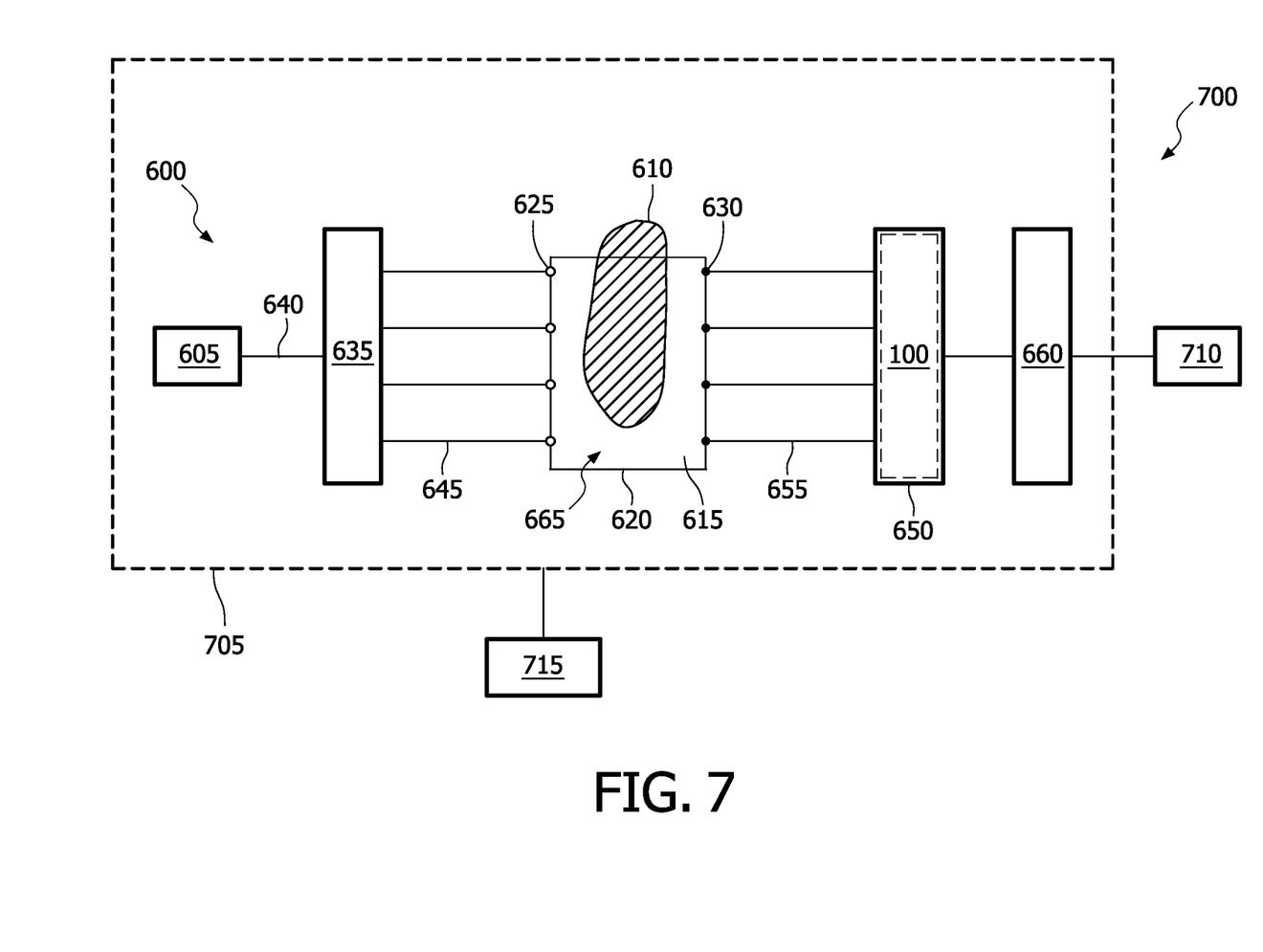
FIG. 7 schematically shows an embodiment of a medical image acquisition device comprising a determination circuit according to the invention.
Figure 8:
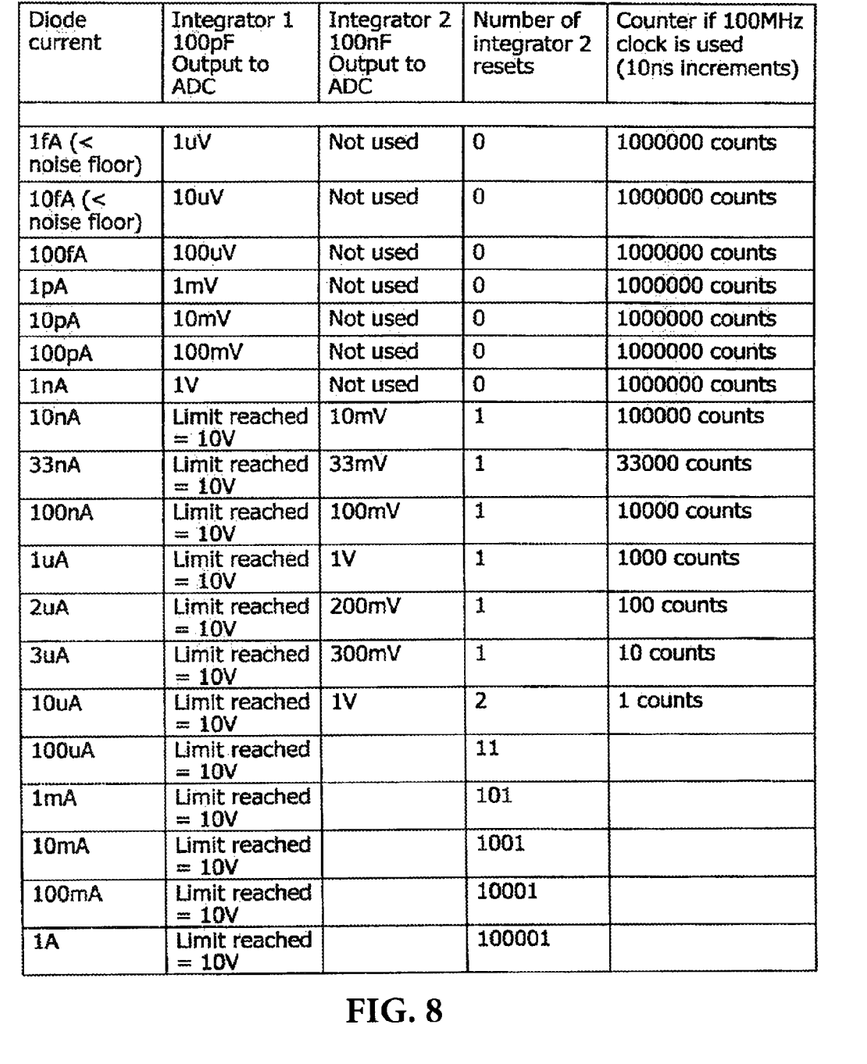
FIG. 8 lists current measurements using only the higher gain circuit, only the lower gain circuit, or both circuits.

FIG. 7 schematically shows an embodiment of a medical image acquisition device comprising a determination circuit according to the invention. The medical image acquisition device 700 comprises the element is comprised in the device 600 shown in FIG. 6. This is indicated by the dashed rectangle 705. The medical image acquisition device 700 further comprises a screen 710 for displaying a reconstructed image of an interior of the turbid medium 610 and an operator interface 715, for instance a keyboard, allowing an operator to interact with the medical image acquisition device 700.

Table 1 lists current measurements using only the higher gain circuit, only the lower gain circuit, or both circuits.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements, and by means of a suitably programmed computer. In the system claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:
1. A determination circuit comprising:
an integration unit for integrating a current over an integration time resulting in an integration value;
a time counter unit for counting the integration time from the start of integrating the current to a predefined maximum integration time;
a reset counter for counting the number of resets of the integration unit,
wherein the determination circuit is configured to:

output a first measurement result if the absolute value of the integration value is below a reset threshold at the expiration of the predefined maximum integration time;
reset the integration unit if the absolute value of the integration value exceeds the reset threshold before the expiration of the predefined maximum integration time;
repeat the outputting and resetting each time the absolute value of the integration value exceeds the reset threshold until expiration of the maximum integration time, counting the number of resets;
output a second measurement result based on at least one of the integration value and the number of resets if the number of resets is nonzero
wherein the integration unit comprises:
a higher gain integration circuit for integrating the current if the absolute value of the integration value lies below a switching threshold before expiration of the predefined maximum integration time;
a lower gain integration circuit for integrating the current until expiration of the predefined maximum integration time if the absolute value of the integration value generated by the higher gain integration circuit exceeds the switching threshold before expiration of the maximum integration time.

2. A method for measuring a current, the method comprising acts of:
integrating the current over a predefined maximum integration time using an integration unit, resulting in an integration value;
counting the integration time from the start of integrating the current to the expiration of the predefined maximum integration time;
outputting a first measurement result if the absolute value of the integration value is below a reset threshold at the expiration of the predefined maximum integration time;
resetting the integration unit if the absolute value of the integration value exceeds the reset threshold before the expiration of the predefined maximum integration time;
repeating the acts of outputting and resetting each time the absolute value of the integration value exceeds the reset threshold until expiration of the predefined maximum integration time, counting the number of resets;
outputting a second measurement result based on at least one of the integration value and the number of resets if the number of resets is nonzero; and
switching the integration unit from a higher gain setting to a lower gain setting if the absolute value of the integration value generated in the higher gain setting exceeds a switching threshold before expiration of the predefined maximum integration time.

3. A non-transitory computer readable medium comprising computer instructions which, when executed by a processor, configure the processor to perform acts of:
integrating the current over a predefined maximum integration time using an integration unit, resulting in an integration value;
counting the integration time from the start of integrating the current to the expiration of the predefined maximum integration time;
outputting a first measurement result if the absolute value of the integration value is below a reset threshold at the expiration of the predefined maximum integration time;
resetting the integration unit if the absolute value of the integration value exceeds the reset threshold before the expiration of the predefined maximum integration time;
repeating the acts of outputting and resetting each time the absolute value of the integration value exceeds the reset threshold until expiration of the predefined maximum integration time, counting the number of resets;
outputting a second measurement result based on at least one of the integration value and the number of resets if the number of resets is nonzero; and
switching the integration unit from a higher gain setting to a lower gain setting if the absolute value of the integration value generated in the higher gain setting exceeds a switching threshold before expiration of the predefined maximum integration time.

\* \* \* \* \*